(12) United States Patent
Morey et al.

(10) Patent No.: US 12,390,222 B2
(45) Date of Patent: Aug. 19, 2025

(54) REPOSITIONABLE OVER THE SCOPE CLIP (71) Applicant: BOSTON SCIENTIFIC MEDICAL DEVICE LIMITED, Galway (IE)

(72) Inventors: Subodh Morey, Ponda (IN); Rajivkumar Singh, Thane (IN)

(73) Assignee: Boston Scientific Medical Device Limited, Galway (IE)

( * ) Notice: Subject to any disclaimer, the term of this patent is extended or adjusted under 35 U.S.C. 154(b) by 473 days.

(21) Appl. No.: 17/805,950

(22) Filed: Jun. 8, 2022

(65) Prior Publication Data

US 2023/0036540 A1     Feb. 2, 2023

Related U.S. Application Data

(60) Provisional application No. 63/203,802, filed on Jul. 30, 2021.

(51) Int. Cl.
| | |
|---|---|
| *A61B 17/128* | (2006.01) |
| *A61B 17/00* | (2006.01) |
| *A61B 17/064* | (2006.01) |
| *A61B 17/122* | (2006.01) |

(52) U.S. Cl.
CPC ...... *A61B 17/1285* (2013.01); *A61B 17/1227* (2013.01); *A61B 2017/00296* (2013.01); *A61B 2017/00862* (2013.01); *A61B 2017/0641* (2013.01)

(58) Field of Classification Search
CPC .............. A61B 17/1227; A61B 17/128; A61B 17/1285; A61B 2017/00296; A61B 2017/00641

USPC .................................................. 606/142, 143
See application file for complete search history.

(56) References Cited

U.S. PATENT DOCUMENTS

| | | | |
|---|---|---|---|
| 6,066,145 A | 5/2000 | Wurster | |
| 6,607,542 B1 * | 8/2003 | Wild ................. | A61B 17/1222 606/139 |
| 8,303,609 B2 | 11/2012 | Lentz et al. | |
| 10,111,672 B2 | 10/2018 | Smith et al. | |
| 10,722,224 B2 | 7/2020 | Stopek et al. | |

(Continued)

FOREIGN PATENT DOCUMENTS

| | | |
|---|---|---|
| DE | 212018000416 | 1/2021 |
| WO | 2006/136053 | 12/2006 |
| WO | 2015/108926 | 7/2015 |

*Primary Examiner* — Kankindi Rwego
(74) *Attorney, Agent, or Firm* — Fay Kaplun & Marcin, LLP (57) ABSTRACT

A clipping system includes a pusher element, a holder mounted over an insertion device and clips stacked along a length of the holder. The holder includes a longitudinally channel. Each clip extends along a curvature defining a tissue-receiving space therewithin and extends about the holder with an exterior surface of the holder holding the clip open with the first and second ends of the clip separated from one another to receive a tissue therein. Each clip is independently deployable from the holder so that, upon release of the clip from the holder, the clip reverts to a closed configuration. In the closed configuration, the first and second ends are moved toward one another to reduce a size of the tissue-receiving space so that tissue is gripped therewithin. The element is mounted over the holder and moved distally along the holder to independently deploy each clips.

10 Claims, 3 Drawing Sheets

(56) References Cited

U.S. PATENT DOCUMENTS

| | | |
|---|---|---|
| 10,743,854 B2 | 8/2020 | Whitman et al. |
| 2004/0006256 A1 | 1/2004 | Suzuki et al. |
| 2008/0319475 A1 | 12/2008 | Clark et al. |
| 2011/0230897 A1 | 9/2011 | Palermo et al. |
| 2013/0138125 A1 | 5/2013 | Gonzales et al. |
| 2014/0379004 A1 | 12/2014 | Raybin et al. |
| 2015/0201946 A1* | 7/2015 | Shepard ............ A61B 17/0682 606/142 |
| 2016/0128680 A1 | 5/2016 | Voss |
| 2016/0361066 A1 | 12/2016 | Wolfe |
| 2020/0360022 A1 | 11/2020 | Schaubhut et al. |
| 2021/0022740 A1 | 1/2021 | Favreau et al. |

* cited by examiner

REPOSITIONABLE OVER THE SCOPE CLIP

PRIORITY CLAIM

The present disclosure claims priority to U.S. Provisional Patent Application Ser. No. 63/203,802 filed Jul. 30, 2021; the disclosure of which is incorporated herewith by reference.

FIELD

The present disclosure relates to endoscopic devices and, in particular, relates to endoscopic clipping devices for treating tissue along the gastrointestinal tract.

BACKGROUND

Physicians have become more willing to perform aggressive interventional and therapeutic endoscopic gastrointestinal (GI) procedures, which may increase the risk of perforating the wall of the GI tract or may require closure of the GI tract wall as part of the procedure. Such procedures may include, for example, the removal of large lesions, tunneling under the mucosal layer of the GI tract to treat issues below the mucosa, full thickness removal of tissue, treatment of issues on other organs by passing outside of the GI tract, and endoscopic treatment/repair of post-surgical issues (e.g., post-surgical leaks, breakdown of surgical staple lines, and anastomotic leaks). Currently, tissue may be treated via endoscopic closure devices including through-the scope clips or over-the-scope clips. Over-the-scope clips may be particularly useful for achieving closure of larger tissue defects. These endoscopic closure devices can save costs for the hospital and may provide benefits for the patient.

In some cases, however, current endoscopic closure devices may be difficult to use, time consuming to position, or insufficient for certain perforations, conditions and anatomies. For example, current over-the-scope clips generally require launching of the clip from a position in which the clip itself is not visible to the operator. That is, prior to clipping the operator may view the target tissue to be clipped and, based on this visualization of the target tissue, may determine that the distal end of the device and the clip are in a desired position relative to the target tissue. Based on the observation of the target tissue, the operator then deploys the clip without being able to see the clip itself until it is deployed. In addition, current over-the scope clips devices are only able to place one clip upon insertion of the endoscope into the body. In order to place a second clip, the operator must remove the endoscope after deployment of the first clip, reload the endoscope with a new clip, and reinsert the endoscope to a target site to position and deploy the second clip over a target tissue.

SUMMARY

The present disclosure relates to a clipping system for treating tissue which includes a holder configured to be mounted over a distal end of an insertion device, the holder extending longitudinally from a proximal end to a distal end and including a channel extending longitudinally therethrough; a plurality of clips mountable over the holder so that the plurality of clips are stacked along a length thereof, each clip extending along a curvature from a first end to a second end, the curvature defining a tissue-receiving space therewithin, each clip mountable over the holder so that the clip extends about the holder and an exterior surface of the holder holds the clip in an open configuration, in which first and second ends of the clip are separated from one another and the tissue-receiving space is configured to receive a tissue therein, each clip being independently deployable from the holder so that, upon release of the clip from the holder, the clip is permitted to revert to a biased closed configuration, in which the first and second ends are moved toward one another to reduce a size of the tissue-receiving space so that tissue is gripped therewithin; and a pusher element mounted over the holder, proximally of the plurality of clips, the pusher element configured to be moved distally along the holder to independently deploy each of the plurality of clips from the holder, from a distal-most one of the clips to a proximal-most one of the clips.

In an embodiment, the holder is formed of a transparent material.

In an embodiment, the clip includes a plurality of gripping features along an interior surface thereof.

In an embodiment, the gripping features include teeth extending radially into the tissue-receiving space from the interior surface of the clip.

In an embodiment, a distal portion of the holder includes a plurality of longitudinal slots extending therealong and through a wall thereof so that the longitudinal slots are open at the distal end of the holder, the longitudinal slots configured to receive teeth of the clips therein, when the clips are mounted over the holder in the open configuration.

In an embodiment, the pusher element is configured as a ring mounted over the holder so that the pusher element extends about the holder proximally of the proximal-most one of the clips.

In an embodiment, the clip is formed of a shape memory alloy.

In an embodiment, the system further includes a control element extending from a distal end attached to the pusher element and extending distally therefrom along an exterior of the holder and received within a distal opening of the insertion device so that the control element extends proximally through a channel of the insertion device so that, when the control element is drawn proximally relative to the insertion device, the pusher element is moved distally relative to the holder to push the distal-most one of the clips off of the holder.

In addition, the present disclosure relates to a tissue clipping system which includes an endoscope including extending longitudinally from a proximal end to a distal end; a transparent holder extending longitudinally from a proximal end to a distal end and including a channel extending longitudinally therethrough, the holder mounted to the distal end of the endoscope so that the channel of the holder is substantially aligned with a longitudinal axis of the endoscope, the holder including a proximal portion configured to be coupled to an endoscopic shaft and a distal portion extending distally past the distal end of the endoscope; a plurality of clips mountable over the distal portion of the holder so that the plurality of clips are stacked along a length thereof and visible via a visualization system of the endoscope, each clip extending along a curvature from a first end to a second end, the curvature defining a tissue-receiving space therewithin, each clip mountable over the holder so that the clip extends about the holder and an exterior surface of the holder holds the clip in an open configuration, in which first and second ends of the clip are separated from one another and the tissue-receiving space is configured to receive a tissue therein, each clip being independently deployable from the holder so that, upon release of the clip from the holder, the clip is permitted to revert to a biased closed configuration, in which the first and second ends are moved toward one another to reduce a size of the tissue-receiving space so that tissue is gripped therewithin; and a pusher element mounted over the holder, proximally of the plurality of clips, the pusher element configured to be moved distally along the holder to independently deploy each of the plurality of clips from the holder, from a distal-most one of the clips to a proximal-most one of the clips.

In an embodiment, each clip is formed of a shape memory alloy biasing the clip toward the closed configuration so that, when the clip is pushed distally off of the holder, the clip reverts toward the closed configuration.

In an embodiment, each clip includes teeth extending radially into the tissue-receiving space from an interior surface of the clip to facilitate gripping of tissue therewithin.

In an embodiment, a distal portion of the holder includes a plurality of longitudinal slots extending therealong and through a wall thereof so that the longitudinal slots are open at the distal end of the holder, the longitudinal slots configured to receive teeth of the clips therein, when the clips are mounted over the holder in the open configuration.

In an embodiment, the system further includes a control element extending from a distal end attached to the pusher element and extending distally therefrom along an exterior of the holder and received within a distal opening of an insertion device so that the control element extends proximally through a channel of the insertion device to a proximal end accessible to a user of the system.

In an embodiment, the system further includes an actuator assembly including a handle member attached to the proximal end of the endoscope and a wheel rotatably attached to the handle member, a proximal end of a control member connected to the wheel so that a rotation of the wheel moves the control element proximally relative to the endoscope to move the pusher element distally relative to the holder.

In an embodiment, the wheel is connected to the handle member via a ratchet mechanism so that rotation of the wheel relative to the handle member along one ratchet tooth corresponds to a deployment of a single clip from the holder.

Furthermore, the present disclosure relates to a method for clipping tissue which includes inserting an endoscope to a target area within a body lumen and positioning a distal end of the endoscope over a first target tissue, a plurality of clips mounted over the distal end of the endoscope via a transparent holder, the plurality of clips mounted over the holder so that the plurality of clips are stacked along a length thereof and visible via a visualization system of the endoscope, each clip extending along a curvature from a first end to a second end and mounted over the holder in an open configuration, in which first and second ends of the clip are separated from one another and a tissue-receiving space defined via the curvature is configured to receive a tissue therein; applying a suction force through a working channel of the endoscope so that the first target tissue is drawn into a channel of the holder and within the tissue-receiving space of a first distal-most one of the clips; determining whether the first clip is in a desired position relative to the first target tissue; and pushing the plurality of clips distally along the holder via a pusher element positioned proximally of the plurality of clips until the first clip is pushed distally off of the holder, reverting to a biased closed configuration in which the first and second ends are drawn toward one another to reduce a size of the tissue-receiving space so that the first target tissue is gripped therewithin.

In an embodiment, the method further includes repositioning the distal end of the endoscope relative to the first target tissue if it is determined that the first clip is not in a desired position relative to the first target tissue.

In an embodiment, the pusher element is moved distally along the holder by drawing a control member proximally relative to the endoscope, the control member extending distally from a distal end attached to the pusher element along an exterior of the holder and received within a distal opening of the endoscope so that the control member extends proximally through a channel of the endoscope.

In an embodiment, movement of the control member is actuated via an actuator assembly including a handle member attached to the proximal end of the endoscope and a wheel rotatably attached to the handle member via a ratchet mechanism, the proximal end of the control member connected to the wheel so that a rotation of the wheel along one ratchet tooth corresponds to a deployment of a single clip from the holder.

In an embodiment, the method further includes positioning the distal end of the endoscope over a second target tissue; applying a suction force through the working channel of the endoscope so that the second target tissue is drawn into the channel of the holder and within the tissue-receiving space of a second, currently distal-most clip; determining whether the second clip is in a desired position relative to the second target tissue; and pushing the plurality of clips distally along the holder via a pusher element positioned proximally of the plurality of clips until the second clip is pushed distally off of the holder, reverting to a biased closed configuration in which the first and second ends of the second clip are drawn toward one another to reduce a size of the tissue-receiving space of the second clip so that the second target tissue is gripped therewithin.

BRIEF DESCRIPTION

DETAILED DESCRIPTION

The present disclosure may be further understood with reference to the following description and the appended drawings, wherein like elements are referred to with the same reference numerals. The present disclosure relates to a clipping system and, in particular, relates to an over-the-scope endoscopic clipping system, in which multiple clips may be placed to treat multiple tissue defects and/or a larger tissue defect without having to remove the endoscope for reloading of a clip. Exemplary embodiments of the present disclosure comprise a plurality of clips mountable over a distal end of an endoscope via a clip holder that is coupled to a distal end of the endoscope so that each of the clips is independently releasable therefrom. Each of the clips may be configured, for example, as a tensile C-shaped circlip in which ends thereof are separated from one another when the clip is in in the open configuration and drawn toward one another or even drawn past one another so that the sides of the clip overlap when the clip is drawn a closed configuration (e.g., under its natural bias). Each of the clips is mountable over the clip holder so that an exterior surface of the clip holder holds each of the clips in the open configuration.

In this open configuration, each clip extends about the clip holder with the clips aligned sequentially along the length of the clip holder. In use, an endoscope including the clip holder is inserted to a target site of the body (e.g., through a natural body lumen accessed via a naturally occurring bodily orifice) until the distal end of the clip holder is positioned adjacent to a first target portion of tissue. The clip holder may be transparent so that a position of the clips relative to the first target tissue may be visualized through the open distal end of the clip holder and through the side wall of the clip holder via the optical system of the endoscope. Upon confirmation that the first target portion of tissue is in a desired position relative to the clip holder, the first target portion of tissue is drawn into the clip holder (e.g., using suction or a grasper inserted through a working channel of the endoscope), a distal-most first one of the clips is moved distally off of the clip holder so that, as the first clip reverts toward the closed configuration under its natural bias, it closes over the first target portion of tissue that had been drawn into the clip holder.

In the closed configuration, the ends of the clip are drawn toward one another, reducing a size of the space within the clip (e.g., a space defined radially within the curvature of the clip) so that the first target portion of tissue is clipped via the first clip within this reduced space. In particular, the first target portion of tissue is encircled and compressed by the clip. The distal end of the endoscope may then be positioned adjacent to a second target portion of tissue, as desired. The second target portion of tissue may then be drawn into the clip holder and a second (now distal-most) clip is then drawn distally off of the clip holder so that the second clip closes over the second target portion of tissue. This process may be repeated until each of the clips has been deployed over a respective target portion of tissue or until all of the target portions of tissue have been clipped as desired. It will be understood by those of skill in the art that terms proximal and distal, as used herein, are intended to refer to a direction toward and away from, respectively, a user of the device.

FIGS. 1-10 show a clipping system 100 for treating tissue defects and/or perforations according to an exemplary embodiment of the present disclosure. The clipping system 100 comprises a plurality of clips 102 configured to be mounted over a clip holder 108 configured to be mounted to distal end 106 of an endoscope 104 or other insertion device configured to be inserted through intervening anatomy to reach a target site within the body at which tissue to be clipped is located. The clips 102 of this embodiment are independently releasable from the holder 108 so that each clip 102 may be deployed to a separate corresponding target portion of tissue allowing the multiple clips 102 to be deployed to treat multiple tissue defects and/or multiple separated parts of a larger tissue defect.

Each of the clips 102 is curved from a first end 112 to a second end 114 and is movable between an open configuration, in which the first and second ends 112, 114 are separated from one another so that tissue may be received within a space 116 defined within the curvature of the clip 102, and a closed configuration, in which the first and second ends 112,114 are drawn toward one another so that an area of the space 116 defined via the curvature is reduced to grip tissue therein. The clips 102 of this embodiment are biased toward the closed configuration and the clip holder 108 is sized so that, when the clips 102 are mounted over the holder 108, an exterior surface 118 of the holder 108 holds each of the clips 102 spread open into the open configuration. In one exemplary embodiment, each of the clips 102 extends about a perimeter (e.g., diameter) of the holder 108 and the clips 102 are positioned sequentially along a length of the holder 108 from a first distal-most one of the clips 102 to a proximal-most one of the clips 102.

In one embodiment, the holder 108 is formed of a transparent material so that, when tissue is drawn into a channel 174 of the clip holder 108 (e.g., via suction or a tissue grasper applied though a working channel of the endoscope 104), and the tissue is drawn into the space 116, the tissue and the position of the clips 102 relative thereto may be visualized through the channel 174 and through the clip holder 108 using a visualization system of the endoscope 104. If, upon visualization, an operator of the system (e.g., surgeon) determines that the clips 102 are in a desired position relative to a target tissue, the first distal-most one of the clips 102 is deployed to grip the target tissue that has been drawn into the channel 174. If the user determines at this point that the first target portion of tissue is not positioned as desired the clip holder 108 may be repositioned until the proper positioning is achieved.

When the proper positioning is achieved and the first target portion of tissue is drawn into the holder 108 as desired, in one embodiment, the pusher element 110, which is positioned along the holder 108 proximally of the proximal-most one of the clips 102, is moved distally relative to the holder 108 to push the proximal-most clip 102 distally along the holder 108. This distally directed pushing force is transmitted sequentially via the intervening clips 102 until the first distal-most clip 102 is pushed distally off of the distal end of the clip holder 108. When the first distal-most clip 102 is moved distally off of the holder 108, the first distal-most clip 102 is freed to revert, under its natural bias, to the closed configuration in which it radially compresses about and grips the first target portion of tissue. The gripped first target portion of tissue may then be released (e.g., by discontinuing the suction or releasing the grasper), endoscope 104 may then be moved to a different area within the target site until the clip holder 108 is adjacent to a second target portion of tissue.

Figure 8:
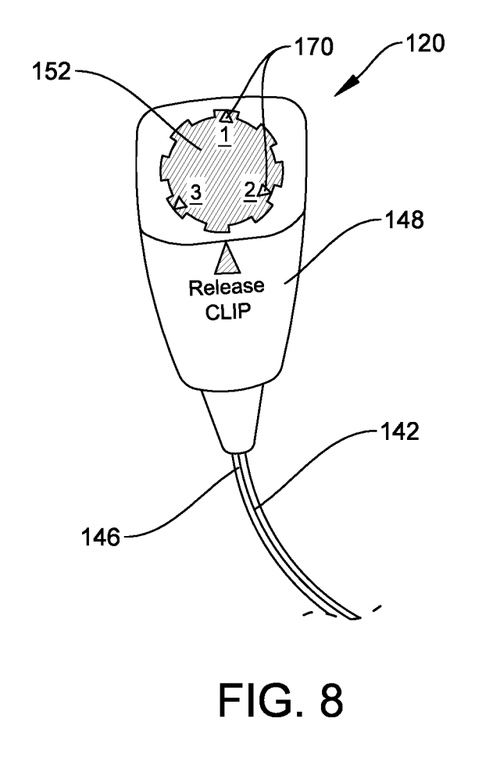
FIG. 8 shows a side view of an actuator assembly according to the system of FIG. 1.
Figure 9:
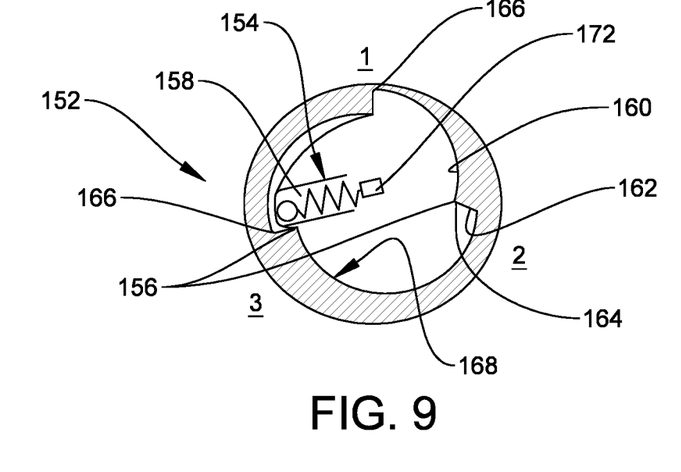
FIG. 9 shows a cross-sectional view of a wheel of the actuator assembly of FIG. 8.

The second target portion of tissue may then be drawn into the holder 108 as described above and a second (now distal-most) clip 102 may be deployed to clip this second target portion of tissue in the same manner described above for the first clip 102. This process may be repeated, as necessary until the target site has been treated, as desired or until all of the available clips 102 have been deployed. As will be described in further detail below and as shown in FIGS. 8 and 9, the pusher element 110 may be actuated via an actuator assembly 120 at a proximal end 146 of the endoscope 104.

Clip holders 108 may be configured in a variety of sizes and/or shapes so that they may be mounted over the distal ends 106 of any number of endoscopes 104, via, for example, a friction fit. As will be understood by those of skill in the art, the endoscope 104 is an elongated, flexible shaft configured to be inserted through a body lumen to a target area within the body (and may even be passed out of the lumen to reach target sites external to the lumen in, e.g., NOTES procedures) and thus, must be sufficiently flexible to navigate through even tortuous paths of the body lumen to reach a target site. In an exemplary embodiment, the holder 108 extends longitudinally from a proximal end 122 to a distal end 124 and includes a channel 174 extending longitudinally therethrough to a distal opening into which target tissue to be clipped may be drawn.

Figure 1:
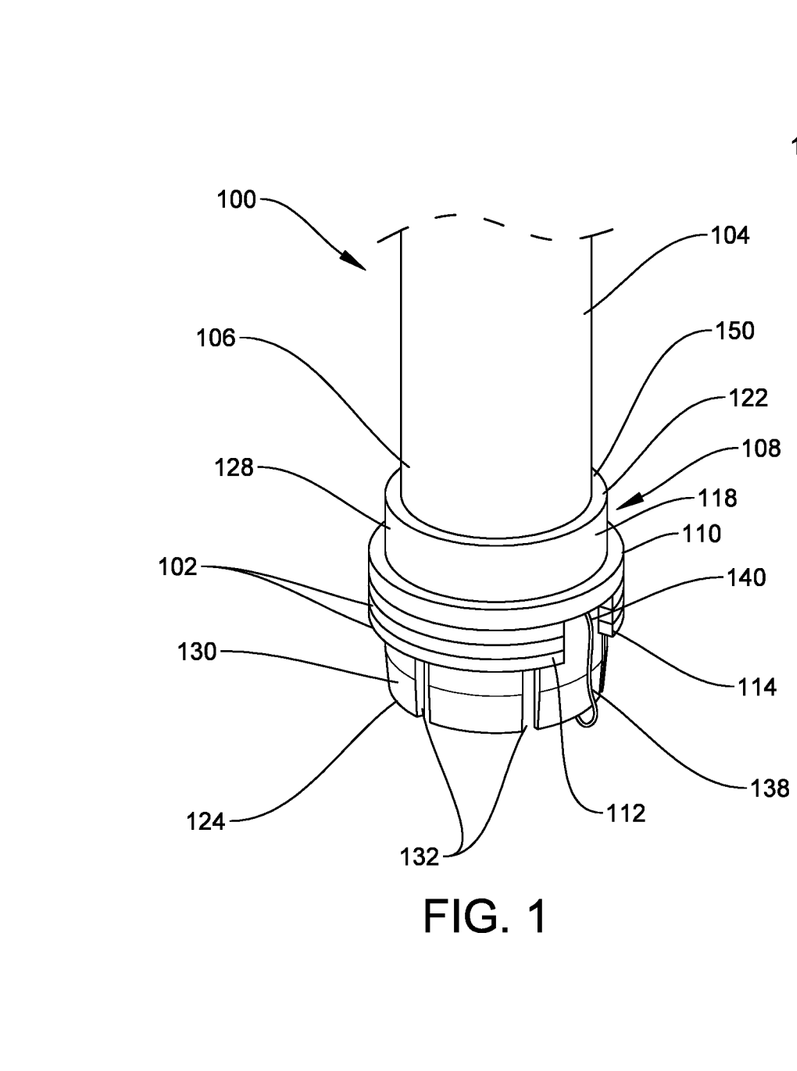
FIG. 1 shows a perspective view of a distal portion of a system according to an exemplary embodiment of the present disclosure.
Figure 2:
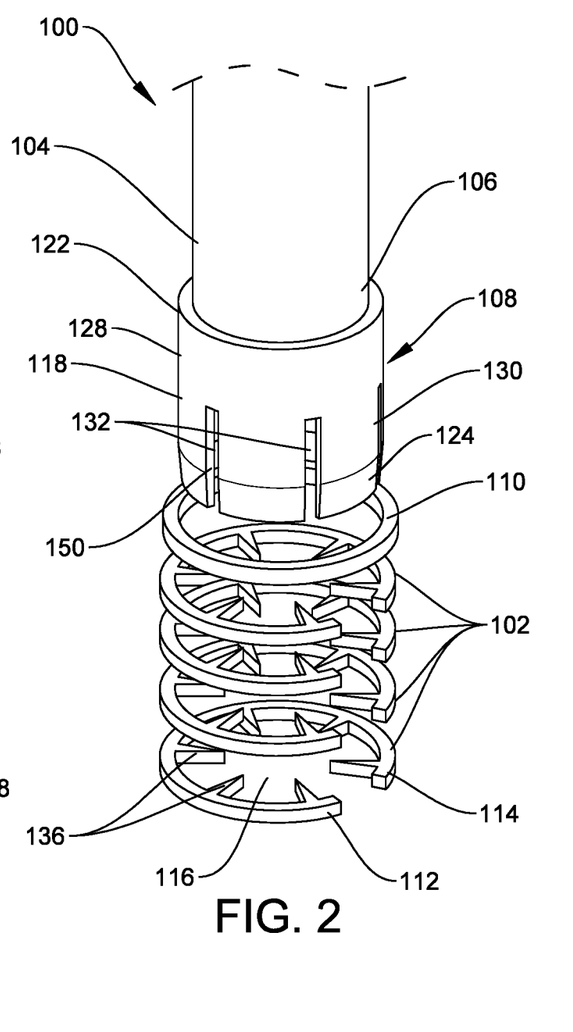
FIG. 2 shows an exploded perspective view of the distal portion of the system of FIG. 1.

As shown in FIGS. 1 and 2, the holder 108 is configured to be mounted to the distal end 106 of the endoscope 104 so that, when the holder 108 is mounted thereon, the channel 174 of the holder 108 is substantially aligned with a longitudinal axis of the endoscope 104 and in communication with a working channel 126 of the endoscope 104 (i.e., so that suction or devices passed through the channel 126 will operate within the channel 174. Although exemplary embodiments show and describe the holder 108 as coupled to the endoscope 104, it will be understood by those of skill in the art that, in an alternative embodiment, the holder 108 may be sized and shaped to be mounted over the distal end of any insertion device (flexible or rigid) suitable for accessing a target site within a body at which a tissue to be clipped is located.

As described above, in one embodiment, the holder 108 is formed of a transparent material so that, when clips 102 are mounted over the distal end 106 of the endoscope 104 via the holder 108, all, several of, or at least the distal-most one of the clips 102 is (are) within a field of view of the endoscope 104. In one embodiment, the holder 108 is substantially cylindrical. It will be understood by those of skill in the art, however, that the holder 108 may have any of a variety of shapes and sizes so long as the holder 108 is configured to be mounted over the distal end 106 of the endoscope 104 or other insertion device and that the channel 174 is sufficiently sized to permit the entry therein of a desired portion of tissue to be clipped.

Figure 3:
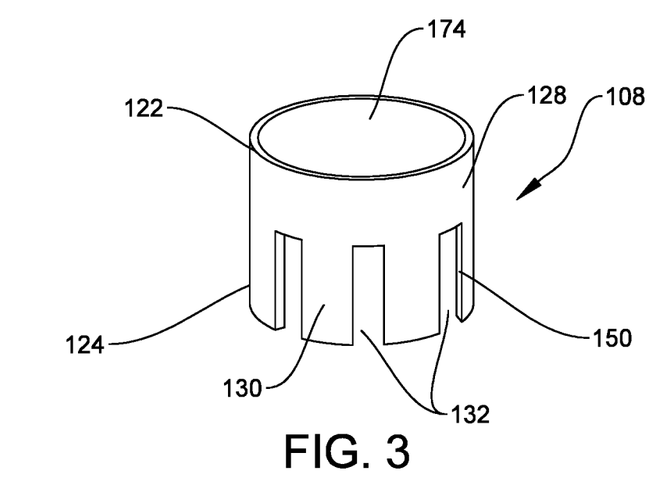
FIG. 3 shows a perspective view of a holder according to the system of FIG. 1.

In one exemplary embodiment, a proximal portion 128 of the holder 108 is configured to be mounted over the distal end 106 of the endoscope 104 while a distal portion 130 of the holder 108 extends distally past the distal end 106. Thus, some or all of the clips 102 mounted over the distal portion 130 are within the field of view of the endoscope 104 and visible to the operator of the system 100 through a wall 150 of the holder 108 via the visualization system of the endoscope 104. As also shown in FIG. 3, the distal portion 130 may include longitudinal slots 132 extending longitudinally therealong through the wall 150 of the holder 108 so that the slots 132 are in communication with the channel 174 of the holder 108 and open to the outside of the wall 150 as well as at the distal end 124 of the holder 108. In one embodiment, each of the slots 132 is equidistantly spaced relative to one another about a circumference of the holder 108. It will be understood by those of skill in the art, however, that the slots 132 may have any of a variety of spacings relative to one another so long as the slots 132 engage the clips 102 to guide them as they move distally over the holder 108, as will be described in further detail below.

Figure 4:
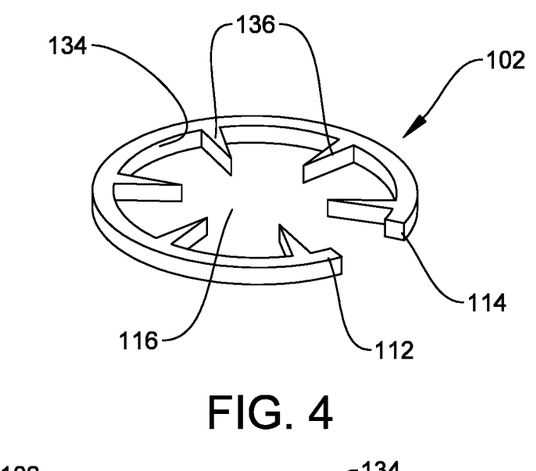
FIG. 4 shows a perspective view of a clip according to the system of FIG. 1.
Figure 5:
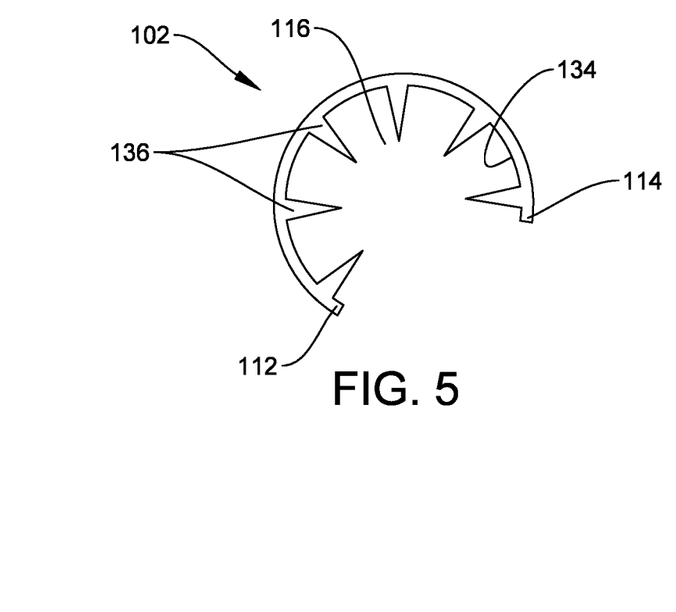
FIG. 5 shows a plan view of the clip of FIG. 4, in an open configuration.
Figure 6:
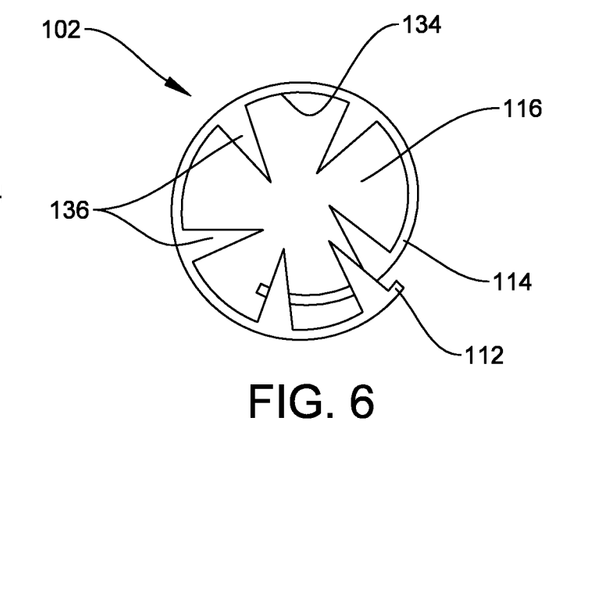
FIG. 6 shows a plan view of the clip of FIG. 4, in a closed configuration.

As shown in FIGS. 4-6, each of the clips 102 extends along a curvature from the first end 112 to the second end 114 and, in one exemplary embodiment, is a substantially C-shaped circlip. The curvature of the clip 102 defines the space 116 within which target tissue may be received when the clip 102 is in the open configuration (as shown in FIGS. 4 and 5). Thus, when the clip is pushed off of the holder 108, the clip 102 closes (as shown in FIG. 6) to grip/clip the tissue that had been drawn therethrough. In other words, the clip 102 is configured to be expanded to receive and substantially encircle target tissue drawn therethrough so that, when the clip 102 is released this target tissue is clipped by the radially contracting clip 102. As described above, the clips 102 of one embodiment are formed of an elastic or tensile material biased toward the closed configuration. In one embodiment, the clip 102 may be formed of a shape memory alloy such as, for example, Nitinol. As also described above, when received on the holder 108, the clip 102 is held in the open configuration via the exterior surface 118 of the holder 108.

For example, in one embodiment, an outer diameter of the holder 108 is selected to be larger than a diameter of the space 116 when the clip 102 has reverted to the biased closed configuration. Thus, when the clip 102 is mounted over the holder 108, the clip 102 is stretched and held in the open configuration. In one embodiment, in the open configuration, the first and second ends 112, 114 are separated from one another although those skilled in the art will understand that this is not necessary. In this open configuration, the space 116 defined via the curvature of the clip 102 is sized to permit tissue to be received therein.

In one embodiment, in the closed configuration, the first and second ends 112, 114 are moved toward one another until they come into contact with one another, substantially forming a closed ring. In another embodiment, when the clip 102 closes, the first and second ends 112, 114 move past one another so that the sides of the clip 102 that are separated in the open configuration overlap one another to form an even smaller space 116. In yet another embodiment, the first and second ends 112, 114 are moved toward one another, but do not come into contact with one another.

One or more of the clips 102 may also include radially inwardly facing gripping features 136 which, when the clip 102 closes over target tissue, contact the target tissue in a manner that facilitates or enhances a gripping of tissue received within the space 116 making the clip 102 more secure in its position clipped over the target tissue. The gripping features 136 may include, for example, one or more teeth 136 extending radially inwardly from an interior surface 134 thereof. In one embodiment, the teeth 136 are equally spaced from one another circumferentially about an inner diameter of the clip 102. In another embodiment, adjacent ones of the teeth 136 are variably spaced about the inner circumference of the clip 102 in any manner deemed effective to enable the teeth 136 to grip tissue received within the space 116. Although the exemplary embodiments show and describe the gripping features 136 as teeth, it will be understood by those of skill in the art that the gripping features may include any of a variety of configurations such as, for example, other protrusions or a roughened interior surface 134, so long as the features facilitate gripping of tissue received within the space 116.

As described above, the clips 102 are mounted over the holder 108 stretched and held in the open configuration so that each clip 102 extends about the holder 108 and the clips 102 are stacked sequentially along a length of the holder 108. In one embodiment, the clips 102 are mounted over the distal portion 130 so that each of the teeth 136 of each of the clips 102 extends through a corresponding one of the longitudinal slots 132. In particular, each clip 102 extends about the exterior 118 of the holder 108 with each of the teeth 136 extending radially inward through a corresponding one of the longitudinal slots 132 into the channel 174 of the holder 108. This helps guide the proximal to distal movement of the clips 102 as the distal-most clip is pushed distally by the series of clips 102 mounted proximally thereto. In one embodiment, positions of the teeth 136 relative to a portion of tissue suctioned into the channel 174 are also visible via the endoscope 104. In one embodiment, the clips 102 are aligned relative to one another so that, for example, the first ends 112 and the second ends 114 of the clips 102 are aligned (i.e., at substantially the same positions circumferentially about the holder 108) along a length of the holder 108.

The pusher element 110 also extends about the holder 108. The pusher element 110, however, extends proximally of a proximal-most one of the clips 102. In one embodiment, the pusher element 110 is configured as a ring extending about the holder 108 abutting the proximal-most one of the clips 102. Thus, when the pusher element 110 is moved distally relative to the holder 108, the proximal-most clip 102 is pushed distally against the next most proximal clip 102 which pushes against the distally adjacent clip, etc., until the force is applied to the distal-most clip 102 by the second most distal of the clips 102. The user can observe the motion of the clips 102 along the holder 108 so that the user can see when the distal-most clip is pushed distally off of the holder 108 to clip tissue that had been drawn into the channel 174.

When it is desired to deploy one of the clips 102, the user operates the actuator assembly 120 to push the pusher element 110 distally relative to the holder 108 over a specific distance selected to only push one clip 102 (i.e., a distal-most one of the clips 102 on the holder 108) off of the holder 108. That is, for example, a stroke of the actuator assembly is selected so that actuation of the assembly 120 through its complete range of motion (or through a single deployment range of motion of the actuator assembly 120) corresponds to a range of motion of the pusher element 110 required to deploy a single one of the clips 102. The same process may be repeated for each clip 102 when a new portion of tissue has been drawn into the channel 174 so that operation of the actuator assembly 120 allows an operator to generate a controlled movement of the pusher element 110 that deploys one and only one clip 102 at a time.

Figure 7:
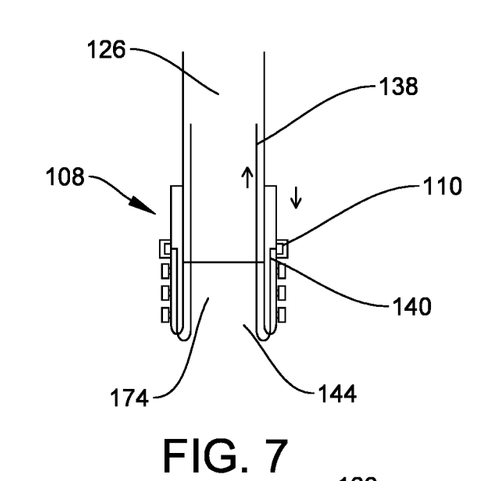
FIG. 7 shows a longitudinal cross-sectional view of a distal portion of the system of FIG. 1.

As shown in FIG. 7, movement of the pusher element 110 is controlled via a control element 138, which, in one embodiment, is configured as a cable, strand, thread, wire or other longitudinally extending element. In one exemplary embodiment, the control element 138 extends from a distal end 140 attached to the pusher element 110 to a proximal end 142 connected to the actuator assembly 120. According to an exemplary embodiment, the control element 138 extends distally from the pusher element 110 along the exterior 118 of the holder 108 so that a remaining length extends through a distal opening 144 of the channel 174 to be passed proximally through the channel 126 of the endoscope 110 to be coupled to the actuator assembly 120. Thus, proximal movement of the control element 138 relative to the endoscope 104 moves the pusher element 110 distally relative to the holder 108 to deploy the clip 102. In one embodiment, the control element 138 extends from the pusher element 110 along the exterior 118, between the first and second ends 112, 114 of the clips 102 so as not to interfere with a deployment of the clips 102.

According to an exemplary embodiment, the actuator assembly 120, as shown in FIGS. 8 and 9, includes a handle member 148 connected to the proximal end 146 of the endoscope 104 and a wheel 152 rotatably coupled to the handle member 148. The proximal end 142 of the control element 138 in this embodiment extends proximally through the endoscope 104 and the handle member 148 to be coupled to the wheel 152 so that, when the wheel 152 is rotated relative to the handle member 148, the control member 138 is moved proximally relative to the endoscope 104 to move the pusher element 110, and thereby the clips 102, distally relative to the holder 108. As those skilled in the art will understand, the actuating assembly 120 may be configured to give an indication (e.g., tactile, auditory or visual) of an amount of motion that corresponds to a range of motion of the pusher element 110 that is required to deploy a single clip 102.

In one embodiment, the wheel 152 is coupled to the handle member 148 via a ratchet mechanism 154 so that the wheel 152 will "click" upon rotation of the wheel 152 relative to the handle member 148 via a specific amount configured to release just one of the clips 102 (i.e., a distal-most clip 102 along the holder 108) from the holder 108. In one example, the wheel 152 includes a plurality of ratchet teeth 156 and is engaged to the handle member 148 via a spring-biased cam 158. The ratchet teeth 156 in this embodiment extend from an interior surface 168 of the wheel 152 toward a center 172 of the wheel 152. Each of the ratchet teeth 156 includes a first sloped surface 160 and a second sloped surface 162 which meet at a point 164 of the tooth 152. A valley 166 is formed between adjacent ones of the teeth 152. The second sloped surface 162 is much steeper than the first sloped surface 160 so that, when the wheel 152 is rotated relative to the handle member 148 in a first direction, the spring-biased cam 158 slides along the first surface 160 and is compressed until the cam 158 moves past the point 164 and along the second surface 162.

Upon rotation of the wheel 152 so that the cam 158 is moved past the point 164, the cam 158 reverts toward its biased configuration, "clicking" as it is received within the valley 166. This "clicking" provides a tactile and/or auditory feedback to the user indicating that the control element 138 has been moved by the specific distance required to deploy just one of the clips 102—e.g., a first distal-most clip 102. This may be confirmed visually by the operator using the vision system of the endoscope as would be understood by those skilled in the art.

When it is desired to deploy another clip 102, the operator of the system 100 again rotates the wheel 152 relative to the handle member 148 in the first direction until the wheel 152 provides a "click" indicating that a second clip 102 (e.g., a current distal-most clip after deployment of the first clip) has been pushed off of the holder 108. This process may be repeated until the target area has been treated, as desired, or until all of the clips 102 have been deployed. The second surface 162 is steep enough so that the second surface 162 engages the cam 158 preventing the wheel 152 from rotating relative to the handle member 148 in a second direction opposite the first direction. Thus, the control element 138 may be moved only proximally relative to the endoscope 104 to move the pusher element 110 distally relative to the holder 108.

In one embodiment, the wheel 152 includes three ratchet teeth 156, equally positioned relative to one another along the interior surface 168 of the wheel 152. It will be understood by those of skill in the art, however, that the wheel 152 may include any number of ratchet teeth 156 so long as the ratchet teeth 156 are configured to engage the cam 158 so that a single "click" corresponds to the deployment of a single, distal-most one of the clips 102 on the clip holder 108. Furthermore, those skilled in the art will understand that the spacing between ratchet teeth 156 may be varied to achieve an equal distal movement of the pusher element 110 with each click. That is, if, as the wheel 152 is rotated a diameter about which the control member 138 is wound increases, it may be desired to slightly reduce the spacing between the second tooth 156 and a third one of the teeth 156 so that the slightly decreased angle of rotation of this increased diameter winds onto the wheel 152 a length of the control member 138 that is equal with each click. While the rotation of the wheel 152 clicks to provide auditory/tactile feedback to the user, the wheel 152 and/or the handle member 148 may also include markings 170 thereon providing a visual indication to the operator of the system 100 when the distal-most clip 102 on the holder 108 has been deployed.

According to an exemplary method for tissue closure utilizing the clipping system 100, the distal end 106 of the endoscope 104 (or other insertion device), including the holder 108 and the clips 102 mounted thereon in the open configuration, is inserted into a living body (e.g., via a body lumen (e.g., GI tract) accessed, for example, by a naturally occurring body orifice) to a target area within the body lumen. The distal end 106 is positioned over a first target portion of tissue to be clipped and a suction force (or a grasper) is applied through the working channel 126 of the endoscope 104 to draw the first target portion of tissue into the channel 174 of the holder 108. Since the clips 102 are stretched about the holder 108 in the open configuration, the tissue drawn into the channel 174 is also within the space 116 defined via the curvature of at least the distal-most one of the clips 102. The operator may then visualize whether first target portion of tissue and the distal-most one of the clips 102 are in a desired position relative to one another. If the clips 102 are not in the desired position, the tissue drawn into the channel 174 is released and a position of the distal end 106 of the endoscope 104 is adjusted relative to the surrounding tissue until the desired first portion of target tissue is drawn into the channel 174.

When the operator determines that the distal-most one of the clips 102 (first clip 102) is in the desired position relative to the first target portion of tissue, the operator moves the actuator assembly 120 to deploy the first clip 102 from the holder 108, as described above. In particular, operation of the actuator assembly 120 draws the control member 138 proximally. In this embodiment, as the control member 138 which extends through the working channel 126 out of the channel 174 around the distal end of the holder 108 to extend back to the pusher element 110 is drawn proximally through the working channel 126, the portion extending proximally to the pusher element 120 is drawn distally over the holder 108 drawing the pusher element 110 distally until the first clip 102 is pushed off of the holder 108. The first clip 102 then reverts to its biased closed configuration around the first target portion of tissue to clip this tissue. The first clip 102 may substantially encircle the first target tissue to grip the tissue within the space 116. As described above, gripping features 136 such as, for example, teeth, facilitate gripping of the tissue when the tissue is clipped via the clip 102.

If upon deployment of the first clip 102 it is determined that there is additional tissue to be clipped, the first portion of target tissue is released and the distal end 106 of the endoscope 104 is positioned over a second target portion of tissue. The second target portion of tissue may then be drawn into the channel 174 of the holder 108 so that the operator may visualize a position of the newly distal-most one of the clips 102 (second clip 102) on the holder 108 relative to the second target portion of tissue. When it is determined that the second clip 102 is in a desired position relative to the second target portion of tissue, the operator again actuates the actuator assembly 120 to push the second clip 102 off the of the holder 108 to clip the second target portion of tissue and this process may be repeated as desired until all of the tissue to be clipped has been clipped or until all of the clips 102 have been deployed.

It will be apparent to those skilled in the art that various modifications may be made in the present disclosure, without departing from the scope of the disclosure.

What is claimed is:

1. A clipping system for treating tissue, comprising:
   a holder configured to be mounted over a distal end of an insertion device, the holder extending longitudinally from a proximal end to a distal end and including a channel extending longitudinally therethrough;
   a plurality of clips mountable over the holder so that the plurality of clips are stacked directly adjacently along a length thereof, each clip of the plurality of clips extending along a curvature from a first end to a second end, the curvature defining a tissue-receiving space therewithin, each clip of the plurality of clips mountable over the holder so that each clip of the plurality of clips extends about the holder and an exterior surface of the holder holds each clip of the plurality of clips in an open configuration, in which the first and second ends of each clip of the plurality of clips are separated from one another and the tissue-receiving space is configured to receive a tissue therein, each clip of the plurality of clips being independently deployable from the holder so that, upon release of each clip of the plurality of clips from the holder, each clip of the plurality of clips is permitted to revert to a biased closed configuration, in which the first and second ends are moved toward one another to reduce a size of the tissue-receiving space so that the tissue is gripped therewithin; and
   a pusher element mounted over the holder, proximally of the plurality of clips, the pusher element configured to be moved distally along the holder to independently deploy each of the plurality of clips from the holder, from a distal-most one of the plurality of clips to a proximal-most one of the plurality of clips.

2. The system of claim 1, wherein the holder is formed of a transparent material.

3. The system of claim 1, wherein at least one clip of the plurality of clips includes a plurality of gripping features along an interior surface thereof.

4. The system of claim 3, wherein the gripping features include teeth extending radially into the tissue-receiving space from the interior surface of the at least one clip.

5. The system of claim 1, wherein the pusher element is configured as a ring mounted over the holder so that the pusher element extends about the holder proximally of the proximal-most one of the plurality of clips.

6. The system of claim 1, wherein at least one clip of the plurality of clips is formed of a shape memory alloy.

7. The system of claim 1, further comprising a control element extending from a distal end attached to the pusher element and extending distally therefrom along an exterior of the holder and received within a distal opening of the insertion device so that the control element extends proximally through a channel of the insertion device so that, when the control element is drawn proximally relative to the insertion device, the pusher element is moved distally relative to the holder to push the distal-most one of the plurality of clips off of the holder.

8. The system of claim 1, wherein the pusher element is positioned along the holder proximally of the proximal-most one of the plurality of clips and is configured to move distally relative to the holder to push the proximal-most clip of the plurality of clips distally along the holder to sequentially transmit a force via one or more intervening clips of the plurality of clips until the first distal-most clip of the plurality of clips is pushed distally off of the distal end of the holder.

9. A clipping system for treating tissue, comprising:
a holder configured to be mounted over a distal end of an insertion device, the holder extending longitudinally from a proximal end to a distal end and including a channel extending longitudinally therethrough;
a plurality of clips mountable over the holder so that the plurality of clips are stacked directly adjacently along a length thereof, each clip of the plurality of clips extending along a curvature from a first end to a second end, the curvature defining a tissue-receiving space therewithin, each clip of the plurality of clips mountable over the holder so that each clip of the plurality of clips extends about the holder and an exterior surface of the holder holds each clip of the plurality of clips in an open configuration, in which the first and second ends of each clip of the plurality of clips are separated from one another and the tissue-receiving space is configured to receive a tissue therein, each clip of the plurality of clips being independently deployable from the holder so that, upon release of each clip of the plurality of clips from the holder, each clip of the plurality of clips is permitted to revert to a biased closed configuration, in which the first and second ends are moved toward one another to reduce a size of the tissue-receiving space so that the tissue is gripped therewithin; and
a pusher element mounted over the holder, proximally of the plurality of clips, the pusher element configured to be moved distally along the holder to independently deploy each of the plurality of clips from the holder, from a distal-most one of the plurality of clips to a proximal-most one of the plurality of clips, wherein at least one clip of the plurality of clips includes a plurality of gripping features along an interior surface thereof, the gripping features including teeth extending radially into the tissue-receiving space from the interior surface of the at least one clip; and
wherein a distal portion of the holder includes a plurality of longitudinal slots extending therealong and through a wall thereof so that the longitudinal slots are open at the distal end of the holder, the longitudinal slots configured to receive the teeth of the one or more of the plurality of clips therein, when the plurality of clips are mounted over the holder in the open configuration.

10. The system of claim 9, wherein the pusher element is positioned along the holder proximally of the proximal-most one of the plurality of clips and is configured to move distally relative to the holder to push the proximal-most clip of the plurality of clips distally along the holder to sequentially transmit a force via one or more intervening clips of the plurality of clips until the first distal-most clip of the plurality of clips is pushed distally off of the distal end of the holder.

* * * * *